United States Patent
Ueda et al.

(10) Patent No.: US 11,685,975 B2
(45) Date of Patent: Jun. 27, 2023

(54) MAGNESIUM ALLOY

(71) Applicant: Japan Medical Device Technology Co., LTD., Kumamoto (JP)

(72) Inventors: Hironori Ueda, Kumamoto (JP); Masashi Inoue, Kumamoto (JP); Makoto Sasaki, Kumamoto (JP)

(73) Assignee: Japan Medical Device Technology Co., Ltd., Kumamoto (JP)

(*) Notice: Subject to any disclaimer, the term of this patent is extended or adjusted under 35 U.S.C. 154(b) by 0 days.

(21) Appl. No.: 17/138,492

(22) Filed: Dec. 30, 2020

(65) Prior Publication Data

US 2021/0115539 A1    Apr. 22, 2021

Related U.S. Application Data

(63) Continuation of application No. PCT/JP2018/025869, filed on Jul. 9, 2018.

(51) Int. Cl.
| | |
|---|---|
| *C22C 23/04* | (2006.01) |
| *A61L 31/02* | (2006.01) |
| *C22C 1/02* | (2006.01) |
| *C22F 1/06* | (2006.01) |
| *A61L 27/04* | (2006.01) |
| *A61L 31/14* | (2006.01) |
| *A61L 27/50* | (2006.01) |

(52) U.S. Cl.
CPC .............. *C22C 23/04* (2013.01); *A61L 27/047* (2013.01); *A61L 27/50* (2013.01); *A61L 31/022* (2013.01); *A61L 31/14* (2013.01); *C22C 1/02* (2013.01); *C22C 2202/00* (2013.01); *C22F 1/06* (2013.01)

(58) Field of Classification Search
CPC ....... C22C 23/04; C22C 2202/00; C22C 1/02; C22F 1/06; A61L 31/022; A61L 27/04; A61L 29/02
See application file for complete search history.

(56) References Cited

U.S. PATENT DOCUMENTS

| | | |
|---|---|---|
| 5,342,576 A | 8/1994 | Whitehead |
| 6,080,177 A | 6/2000 | Igaki et al. |
| 7,666,351 B2 | 2/2010 | Nishikawa et al. |
| 8,569,333 B2 | 10/2013 | Mollison et al. |

(Continued)

FOREIGN PATENT DOCUMENTS

| | | |
|---|---|---|
| CN | 1809701 A | 7/2006 |
| CN | 101257860 A | 9/2008 |

(Continued)

OTHER PUBLICATIONS

CN-105256213-A: Espacenet English Machine Translation (Year: 2016).*

(Continued)

*Primary Examiner* — Keith Walker
*Assistant Examiner* — Adil A. Siddiqui
(74) *Attorney, Agent, or Firm* — Kagan Binder, PLLC

(57) ABSTRACT

A magnesium alloy containing, in % by mass, 0.95 to 2.00% of Zn, 0.05% or more and less than 0.30% of Zr, 0.05 to 0.20% of Mn, and the balance consisting of Mg and unavoidable impurities, wherein the magnesium alloy has a particle size distribution with an average crystal particle size from 1.0 to 3.0 μm and a standard deviation of 0.7 or smaller.

5 Claims, 2 Drawing Sheets

(56) References Cited

U.S. PATENT DOCUMENTS

| | | | |
|---|---|---|---|
| 9,254,350 | B2 | 2/2016 | Udipi et al. |
| 9,474,637 | B2 | 10/2016 | Zhao |
| 9,510,932 | B2 | 12/2016 | Kumta et al. |
| 9,522,720 | B2 | 12/2016 | Edick |
| 9,593,397 | B2 | 3/2017 | Imwinkelried et al. |
| 10,052,405 | B2 | 8/2018 | Koo et al. |
| 10,196,715 | B2 | 2/2019 | Imwinkelried et al. |
| 10,350,093 | B2 | 7/2019 | Yan et al. |
| 10,478,529 | B2 | 11/2019 | Imwinkelried et al. |
| 2002/0004060 | A1 | 1/2002 | Heublein et al. |
| 2005/0043788 | A1 | 2/2005 | Luo et al. |
| 2006/0130947 | A1 | 6/2006 | Oishi et al. |
| 2007/0135908 | A1 | 6/2007 | Zhao |
| 2007/0231185 | A1 | 10/2007 | Nishikawa et al. |
| 2009/0090479 | A1* | 4/2009 | Westengen .......... B22D 21/007 |
| | | | 164/113 |
| 2009/0116994 | A1* | 5/2009 | Luo ...................... B21C 23/002 |
| | | | 420/405 |
| 2009/0131540 | A1 | 5/2009 | Hiromoto et al. |
| 2010/0145436 | A1 | 6/2010 | Weber et al. |
| 2010/0305684 | A1 | 12/2010 | Kim et al. |
| 2013/0004362 | A1 | 1/2013 | Soba et al. |
| 2013/0090741 | A1 | 4/2013 | Guo et al. |
| 2013/0209195 | A1 | 8/2013 | Kuwabara et al. |
| 2014/0200652 | A1* | 7/2014 | Bayer ...................... C23F 3/03 |
| | | | 623/1.15 |
| 2014/0248288 | A1 | 9/2014 | Kumta et al. |
| 2014/0277396 | A1 | 9/2014 | Mendelson et al. |
| 2015/0196691 | A1 | 7/2015 | Covelli et al. |
| 2016/0022863 | A1* | 1/2016 | Decker ................ A61L 31/022 |
| | | | 606/331 |
| 2016/0022876 | A1 | 1/2016 | Imwinkelried et al. |
| 2016/0024629 | A1 | 1/2016 | Liang et al. |
| 2016/0129162 | A1 | 5/2016 | Pulugurtha et al. |
| 2019/0330718 | A1 | 10/2019 | Ueda et al. |
| 2019/0343666 | A1 | 11/2019 | Sasaki et al. |
| 2020/0139017 | A1 | 5/2020 | Meyer-Kobbe et al. |
| 2021/0001013 | A1 | 1/2021 | Sasaki et al. |

FOREIGN PATENT DOCUMENTS

| | | |
|---|---|---|
| CN | 101468216 A | 7/2009 |
| CN | 101629260 A | 1/2010 |
| CN | 102387825 A | 3/2012 |
| CN | 102548589 A | 7/2012 |
| CN | 102719717 A | 10/2012 |
| CN | 104046867 A | 9/2014 |
| CN | 104498790 A | 4/2015 |
| CN | 104630587 A | 5/2015 |
| CN | 105143483 A | 12/2015 |
| CN | 105256213 A * | 1/2016 |
| CN | 105256213 A | 1/2016 |
| CN | 105586521 A | 5/2016 |
| CN | 107385419 A | 11/2017 |
| CN | 110191971 A | 8/2019 |
| EP | 03482947 A1 | 4/1992 |
| GB | 851871 A | 10/1960 |
| JP | 35018704 B1 | 12/1960 |
| JP | 09256099 A | 9/1997 |
| JP | 2842943 B2 | 1/1999 |
| JP | 2004183062 A | 7/2004 |
| JP | 2005531391 A | 10/2005 |
| JP | 2006087704 A | 4/2006 |
| JP | 2009530039 A | 8/2009 |
| JP | 2010013725 A | 1/2010 |
| JP | 2010503486 A | 2/2010 |
| JP | 2012082474 A | 4/2012 |
| JP | 2013215332 A | 10/2013 |
| JP | 5425364 B2 | 2/2014 |
| JP | 2014534841 A | 12/2014 |
| JP | 5701497 B2 | 4/2015 |
| JP | 2017501756 A | 1/2017 |
| WO | 2006003833 A1 | 1/2006 |
| WO | 2007108450 A1 | 9/2007 |
| WO | 2013052791 A2 | 4/2013 |
| WO | 2014159328 A1 | 10/2014 |
| WO | 2015147184 A1 | 10/2015 |
| WO | 2018122418 A1 | 7/2018 |
| WO | 2018131476 A1 | 7/2018 |
| WO | 2018139647 A1 | 8/2018 |

OTHER PUBLICATIONS

International Search Report, and English Translation thereof, for International Application No. PCT/JP2018/025869, dated Aug. 21, 2018, (2 pages).

Notification of Reasons for Refusal, and English Translation thereof, for Japanese Application No. 2019-555699, dated Dec. 24, 2019, (6 pages).

Decision to Grant, and English Translation thereof, for Japanese Application No. 2019-555699, dated Mar. 10, 2020, (5 pages).

English Abstract for JP2004183062A.

English Abstract for WO2007108450A1.

English Abstract for WO2015147184A1.

English Abstract for WO2018131476A1.

First Chinese Office Action, and English MachineTranslation thereof, for Corresponding Chinese Application No. 201880086293.6, dated Feb. 26, 2021, (15 pages).

First Examination Report for corresponding Indian Patent Application No. 202017054524, dated Apr. 15, 2021, (6 pages).

First Canadian Office Action corresponding Canadian Patent Application No. 3,104,447, dated Apr. 26, 2021, (4 pages).

E-Space English Abstract for CN105143483A.

E-Space English Abstract for CN105256213A.

E-Space English Abstract for CN105586521A.

E-Space English Abstract for CN110191971A.

E-Space English Abstract for CN1809701A.

E-Space English Abstract for CN102719717A.

Yamamoto, "Biomedical Application of Magnesium Alloys," Journal of Japan Institute of Light Metals, vol. 58, No. 11, pp. 570-576, 2008, (13 pages).

Maeda et al., "Fabrication and mechanical properties of biodegradable magnesium stent," Journal of Japan Institute of Light Metals, vol. 66, No. 6, pp. 312-317, 2016, (6 pages).

Mao, L. et al., "Enhanced bioactivity of Mg-Nd-Zn-Zr alloy achieved with nanoscale MgF2 surface for vascular stent application," ACS Appl Mater Interfaces, 2015, vol. 7, No. 9, pp. 5320-5330, abstract, p. 5320, right column, line 2 from the bottom to p. 5321, left column, line 2, section of "Materials and surface modification", (11 Pages).

Liu et al., "Multifunctional MgF2/polydopamine coating on Mg alloy for vascular stent application," Journal of Materials Science and Technology, vol. 31, ISSN: 1005-0302, pp. 733-743, 2015, (11 pages).

Kubota, "Properties of Magnesium Alloys & Their Technology", Journal of the Surface Finishing Society of Japan, vol. 53, No. 3, pp. 8-11, 2002, with machine English translation, (7 pages).

Database Compendex (Online), "Microstructure and properties of Mg-3Zn-0.8Zr-xMn alloy", Database accession No. E20151300692382, Engineering Information, Inc., New York, NY, US, vol. 36, No. 2, pp. 27-31, Feb. 25, 2015, (1 page).

Gui et al., "Mechanical and corrosion properties of Mg·Gd·Zn·Zr·Mn biodegradable alloy by hot extrusion", Journal of Alloys and Compounds, Elsevier Sequoia, Lausanne, CH, vol. 685, pp. 222-230, May 24, 2016, (9 pages).

Extended European Search Report for European Application No. 18926369.2, dated May 18, 2021, (8 pages).

Second Chinese Office Action, and English Translation thereof, for Chinese Application No. 201880086293.6, dated Jul. 23, 2021, (10 pages).

Agarwal et al., "Biodegradable magnesium alloys for orthopaedic applications: A review on corrosion, biocompatibility and surface modifications", Materials Science and Engineering, vol. 68, pp. 948-963, 2016, (27 pages).

E-Space English Abstract for CN101257860A.

E-Space English Abstract for CN101468216A.

(56) References Cited

OTHER PUBLICATIONS

E-Space English Abstract for CN101629260A.
E-Space English Abstract for CN102387825A.
E-Space English Abstract for CN102548589A.
E-Space English Abstract for CN104046867A.
E-Space English Abstract for CN104498790A.
E-Space English Abstract for CN104630587A.
E-Space English Abstract for CN107385419A.
E-Space English Abstract for JP2842943A.
E-Space English Abstract for JP5425364A.
E-Space English Abstract for JP5701497A.
E-Space English Abstract and machine translation for JP09256099A.
E-Space English Abstract and machine translation for JP2005-531391A.
E-Space English Abstract and machine translation for JP2006-087704A.
E-Space English Abstract and machine translation for JP2009-530039A.
E-Space English Abstract for JP2010-013725A.
E-Space English Abstract and machine translation for JP2010-503486A.
E-Space English Abstract JP2012-082474A.
E-Space English Abstract for JP2013-215332A.
E-Space English Abstract and machine translation for JP2014-534841A.
E-Space English Abstract and machine translation for JP2017-501756A.
E-Space English Abstract for WO2018122418A1.
E-Space English Abstract for WO2018139647A1.
Decision on Rejection, and English Translation thereof, for Chinese Application No. 201780082913.4, dated Aug. 31, 2021, (12 pages).
Indian Office Action for Indian Application No. 201917027629, dated Oct. 27, 2021, (6 pages).
"Microstructure and properties", retrieved from 'https://www.researchgate.net/publication/282288987_Microstructureand_properties_of_Mg-sZn-08Zr-xMn_alloy' on Nov. 23, 2021, (4 pages).
Notice of Allowance and Issue Fee Due, U.S. Appl. No. 16/506,298 dated Oct. 1, 2021, (12 pages).
Decision on Rejection, and English Translation thereof, for Chinese Application No. 201880086293.6, dated Nov. 19, 2021, (12 pages).
Chinese Office Action, and English Translation thereof, for Chinese Application No. 202210151600.2 dated Feb. 17, 2023, (13 pages).

\* cited by examiner

MAGNESIUM ALLOY

CROSS REFERENCE TO THE RELATED APPLICATION

This application is a continuation application, under 35 U.S.C. § 111(a), of international application No. PCT/JP2018/025869, filed on Jul. 9, 2018, the entire disclosures of which are herein incorporated by reference as a part of this application.

FIELD OF THE INVENTION

The present invention relates to a magnesium alloy. Specifically, the present invention relates to a magnesium alloy which can be used in applications such as a medical magnesium alloy and has an excellent deformation property.

BACKGROUND OF THE INVENTION

Conventionally, various types of metal devices for medical purposes have been developed, including stents, staplers, and artificial joints. Such metal devices are embedded in a living tissue and remain within a body unless they are removed by surgery. Depending on their purposes, however, it is desired that the metal devices maintain their strength in the body for a certain period of time from the initial phase of implantation and are dissolved and absorbed in the body after repairing of the living tissue. As magnesium is a highly safe metal having low toxicity to the living tissue and is quickly dissolved and absorbed by the body fluid, magnesium and magnesium alloys are being developed for various applications as biodegradable metal materials for medical purposes.

For example, WO 2007/108450 A1 describes a biodegradable magnesium material for medical use which contains magnesium oxides or magnesium hydroxides formed by anodization on crystallized magnesium or a crystallized magnesium alloy. The document also describes that where the magnesium material contains an accessary component other than magnesium, the accessary component is unevenly distributed to crystal grain boundaries at a concentration 1.2 times higher than an average concentration in crystal grains.

Where a magnesium alloy is used as a biodegradable medical material, it is necessary that the alloy maintains its strength until tissue of an affected site is repaired. In the case where the magnesium alloy is in electric contact with a more noble metal, it is preferred to avoid phase separation of a matrix phase in order to avoid rapid galvanic corrosion of the magnesium alloy in contact with the body fluid. In addition, where a magnesium alloy is used as a material for a medical device such as a stent which undergoes deformation, the alloy preferably has suitable deformability (extensibility) and does not contain coarse precipitates (compounds) which may be trigger of a fracture of the alloy after the deformation.

The alloy preferably has uniform crystal particle size in terms of biodegradability, and the particle size can preferably be controlled to fine size so as to enable fine processing of the alloy to a stent or the like.

An object of the present invention is to provide a magnesium alloy having a fine and uniform crystal distribution and excellent deformability.

SUMMARY OF THE INVENTION

A magnesium alloy of the present invention contains, in % by mass, 0.95 to 2.00% of Zn,
0.05% or more and less than 0.30% of Zr,
0.05 to 0.20% of Mn, and
the balance consisting of Mg and unavoidable impurities, wherein
the magnesium alloy has a particle size distribution with an average crystal particle size from 1.0 to 3.0 μm and a standard deviation of 0.7 or smaller.

The magnesium alloy having the above features is composed of substantially single-phase solid solution or has a microstructure in which nanometer-sized fine Zr-bearing precipitates are dispersed in the single-phase alloy. The magnesium alloy has excellent deformability (ductility, elongation ability) because of its fine and uniform particle size and has excellent mechanical properties such as tensile strength and proof strength because of the absence of coarse precipitates at which a fracture starts.

Where the unavoidable impurities of the magnesium alloy include Fe, Ni, Co, and/or Cu, a content of each of Fe, Ni, Co, and Cu being preferably lower than 10 ppm. The magnesium alloy may preferably be free of Co as an unavoidable impurity.

In the magnesium alloy, a total content of the unavoidable impurities may preferably be 30 ppm or lower, and the magnesium alloy preferably does not contain rare-earth elements and aluminum.

The magnesium alloy may have a fracture elongation from 15 to 50% in a value measured in accordance with JIS Z2241. The magnesium alloy may preferably have a fracture elongation exceeding 30%.

The magnesium alloy may have a tensile strength from 250 to 300 MPa and a proof strength from 145 to 220 MPa in values measured in accordance with JIS Z2241.

Preferably, the magnesium alloy does not contain precipitates each having a particle size of 500 nm or larger. More preferably, the magnesium alloy does not contain precipitates each having a particle size of 100 nm or larger.

A medical device of the present invention comprises a metal member containing the above-described magnesium alloy according to the present invention. Since the medical device is made of an alloy having an excellent deformation property, the medical device can stably maintain the shape of the metal member deformed within a body, and the biodegradability of the metal member can be suitably controlled.

The present invention encompasses any combination of at least two features disclosed in the claims and/or the specification and/or the drawings. In particular, any combination of two or more of the appended claims should be equally construed as included within the scope of the present invention.

BRIEF DESCRIPTION OF THE DRAWINGS

The present invention will be more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the figures.

DESCRIPTION OF THE EMBODIMENTS

Hereinafter, an embodiment of the present invention will be described.

Magnesium Alloy

A magnesium alloy of the present invention contains, in % by mass, 0.95 to 2.00% of Zn, 0.05% or more and less than 0.30% of Zr, 0.05 to 0.20% of Mn, and the balance consisting of Mg and unavoidable impurities, wherein the magnesium alloy has a particle size distribution with an average crystal particle size from 1.0 to 3.0 μm and a standard deviation of 0.7 or smaller.

The present invention has revealed that plastic working of the magnesium alloy is improved by controlling a composition of the alloy to the above ranges and that properties of the magnesium alloy such as fracture elongation are improved by achieving fine and uniform particle size of the alloy.

Figure 1:
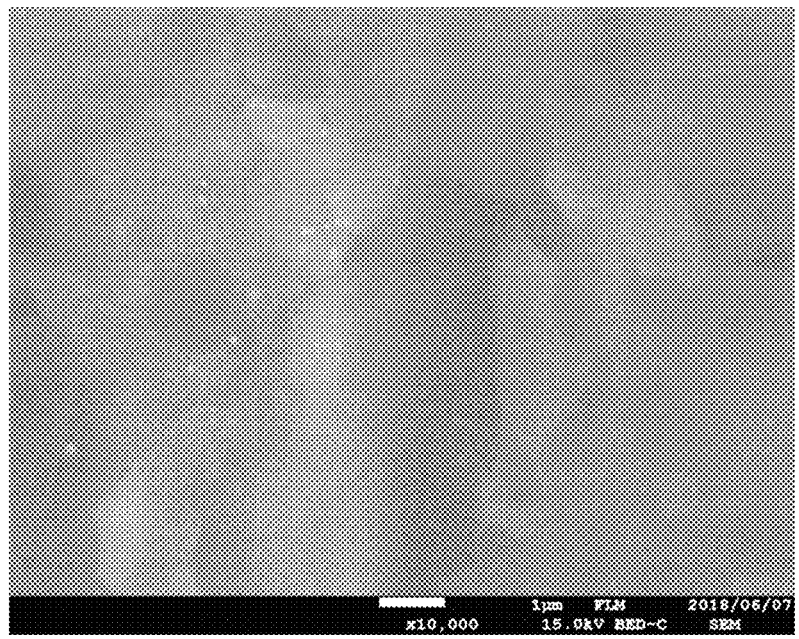
FIG. 1 shows an SEM (scanning electron microscope) image of a microstructure of a magnesium alloy according to Example 1 of the present invention.
Figure 2:
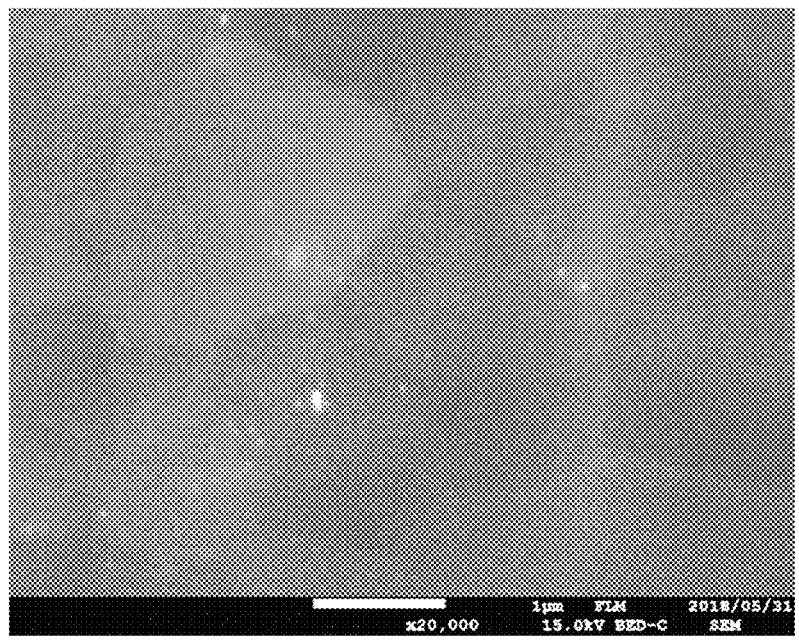
FIG. 2 shows an SEM image of a microstructure of a magnesium alloy according to Example 2 of the present invention.

The magnesium alloy having the above features can avoid formation of coarse precipitates which may be triggers (starting points) of fractures and thereby reduce the possibility of breakage during and after deformation. It should be noted that although Zr, which is added in order to reduce the crystal particle size of the alloy, may form precipitates, the precipitates are typically dispersed at a nanometer scale (in a size smaller than 100 nm) in the matrix phase and thus has a negligible impact on deformation and corrosion of the alloy. For example, FIG. 1 shows an SEM image of an alloy of Example 1, and FIG. 2 shows an SEM image of an alloy of Example 2, as described later. In the figures, the areas having dark contrast show the magnesium alloy (brightness differs among crystal grains), and the white bars at the bottom show a scale of 1 μm. In both of FIG. 1 and FIG. 2, only a few precipitates having particle sizes smaller than 100 nm are observed in some crystal grains of the magnesium alloy, and there are virtually no precipitates in the crystal grain boundaries.

Zinc (Zn): in % by mass, 0.95% or more and 2.00% or less

Zn is added in order to enhance the strength and elongation ability of the alloy by forming a solid solution with Mg. Where the content of Zn is less than 0.95%, a desired effect cannot be obtained. An amount of Zn exceeding 2.00% is not preferred because such an amount may exceed a solid solubility limit of Zn in Mg so that Zn-rich precipitates are formed, resulting in reduced corrosion resistance. For this reason, Zn content is regulated to 0.95% or more and 2.00% or less. The content of Zn may be less than 2.00%.

Zirconium (Zr): in % by mass, 0.05% or more and less than 0.30%

Zr hardly forms a solid solution with Mg and forms fine precipitates, providing an effect of preventing formation of coarse crystal particles of the alloy. Addition of Zr at an amount less than 0.05% cannot provide a sufficient effect. Addition of Zr at an amount equal to or exceeding 0.30% leads to formation of a large amount of precipitates, with a reduced effect of particle size reduction. In addition, corrosion and breakage would start occurring at portions where the precipitates are segregated. For this reason, content of Zr is regulated to 0.05% or more and less than 0.30%. The content of Zr may be 0.10% or more and less than 0.30%.

Manganese (Mn): in % by mass, 0.05% or more and 0.20% or less

Mn allows the alloy to have extremely fine particle size and have improved corrosion resistance. Where an amount of Mn is less than 0.05%, a desired effect cannot be obtained. An amount of Mn exceeding 0.20% is not preferred because plastic workability of the alloy tends to decrease. For this reason, Mn content is regulated to 0.05% or more and 0.20% or less. A preferable content of Mn may be 0.10% or more and 0.20% or less.

Unavoidable Impurities

Preferably, the content of unavoidable impurities is also controlled in the magnesium alloy for medical use. Since Fe, Ni, Co, and Cu promote corrosion of the magnesium alloy, the content of each of these unavoidable impurities is preferably lower than 10 ppm, further preferably 5 ppm or lower, and preferably substantially absent. The total content of the unavoidable impurities is preferably 30 ppm or less, and further preferably 10 ppm or less. Preferably, the magnesium alloy is substantially free from rare-earth elements and aluminum. Where an amount of an impurity element in the alloy is less than 1 ppm, it is regarded that the alloy is substantially free from the impurity element. The amount of impurity may be determined, for example, by ICP optical emission spectrometry.

Production of Magnesium Alloy

In accordance with an ordinal production method of a magnesium alloy, the magnesium alloy may be produced by throwing ground metals or alloys of Mg, Zn, Zr, Mn into a crucible, melting the ground metals and/or alloys in the crucible at a temperature from 650 to 800° C., and casting the molten alloy. Where necessary, the cast alloy may be subjected to solution heat treatment. The ground metals do not contain rare-earth elements (and aluminum). It is possible to suppress the amounts of Fe, Ni, Co, and Cu in the impurities by the use of high purity ground metals. Fe, Ni, and Co in the impurities may be removed by de-ironing treatment to the molten alloy. In addition, or alternatively, it is possible to use ground metals produced by distillation refining.

Metal Microstructure and Mechanical Properties

By the above-described controls of composition and production process, the magnesium alloy can have a fine and uniform structure as seen in a particle size distribution with an average crystal particle size from 1.0 to 3.0 μm (for example, from 1.0 to 2.0 μm) and a standard deviation of 0.7 or smaller (for example, from 0.5 to 0.7). The standard deviation is preferably 0.65 or smaller. Fine precipitates containing Zr may each have a particle size smaller than 500 nm (preferably smaller than 100 nm). A matrix phase excluding the Zr precipitates may preferably be an single-phase solid solution of Mg—Zn—Mn ternary alloy.

The alloy has the following mechanical properties: a tensile strength from 230 to 380 MPa (for example, from 250 to 300 MPa), a proof strength from 145 to 220 MPa, and a fracture elongation from 15 to 50% (for example, from 25 to 40%) in accordance with JIS Z2241. The alloy preferably has a tensile strength exceeding 280 MPa. The alloy preferably has a fracture elongation exceeding 30%.

Medical Device

The magnesium alloy of the present invention has excellent properties as a metal for medical purposes because the alloy has excellent elongation ability and the components of the alloy is controlled to be non-toxic components with non-toxic concentrations for living tissue. The magnesium alloy of the present invention may be suitably used as a metal member constituting a medical device, such as stents, staplers, screws, plates, and coils. For example, the magnesium alloy may be processed to a pipe-shaped member by hot extrusion. The thus-obtained pipe-shaped member may be processed to have a tubular tubular shape by cold-drawing and be further laser-processed to form a stent.

Example

Preparation of Magnesium Alloy

High purity ground metals of Mg, Zn, Mn, and Zr were prepared as initial materials. Each of the metals was weighed so as to have a component concentration as described in Table 1 and was thrown into a crucible. Then, at 730° C. the metals were molten with stirring, and a thus-obtained melt was cast to form ingots. Thus-obtained magnesium alloys of Example 1 and Example 2 contained the main components at formulation ratios which fall within the present invention. The initial materials used did not contain rare earth elements or aluminum even as unavoidable impurities. In this regard, 99.99% pure magnesium ground metal having a low concentration of impurity Cu was used. De-ironing treatment was carried out in the furnace in order to remove iron and nickel from the melt. Concentrations of impurities in the thus-obtained samples were determined using an ICP optical emission spectrometer (AGILENT 720 ICP-OES manufactured by AGILENT). Table 1 shows the compositions of Example 1 and Example 2. The concentrations of Fe, Ni, and Cu were all lower than 8 ppm (Ni and Cu were lower than 3 ppm). Al and the rare-earth elements were not detected, and Co was also below a detection limit. The total content of the unavoidable impurities was 11 ppm.

TABLE 1

| | Component concentration (%) | | | | Impurity concentration (ppm) | | | |
|---|---|---|---|---|---|---|---|---|
| | Mg | Zn | Mn | Zr | Fe | Ni | Cu | Total |
| Example 1 | the balance | 1.86 | 0.14 | 0.12 | 5 | 3 | 3 | 11 |
| Example 2 | the balance | 0.95 | 0.11 | 0.24 | 8 | 3 | 1 | 11 |

Measurement of Mechanical Properties

Each alloy according to the examples was formed into a round bar material through hot extrusion. In accordance with JIS Z2241, a tensile strength, a proof strength, and a fracture elongation of the round bar material were determined. Table 2 shows the results.

Observation of Metal Microstructure

Figure 3:
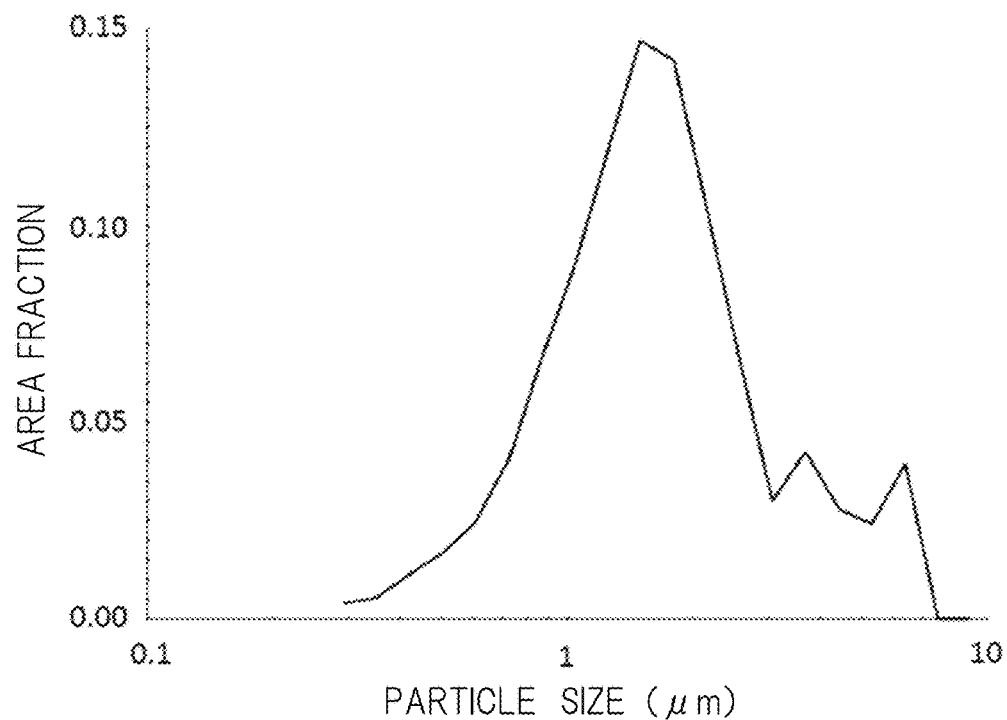
FIG. 3 shows a graph of a particle size distribution of a magnesium alloy according to Example 1 of the present invention.
Figure 4:
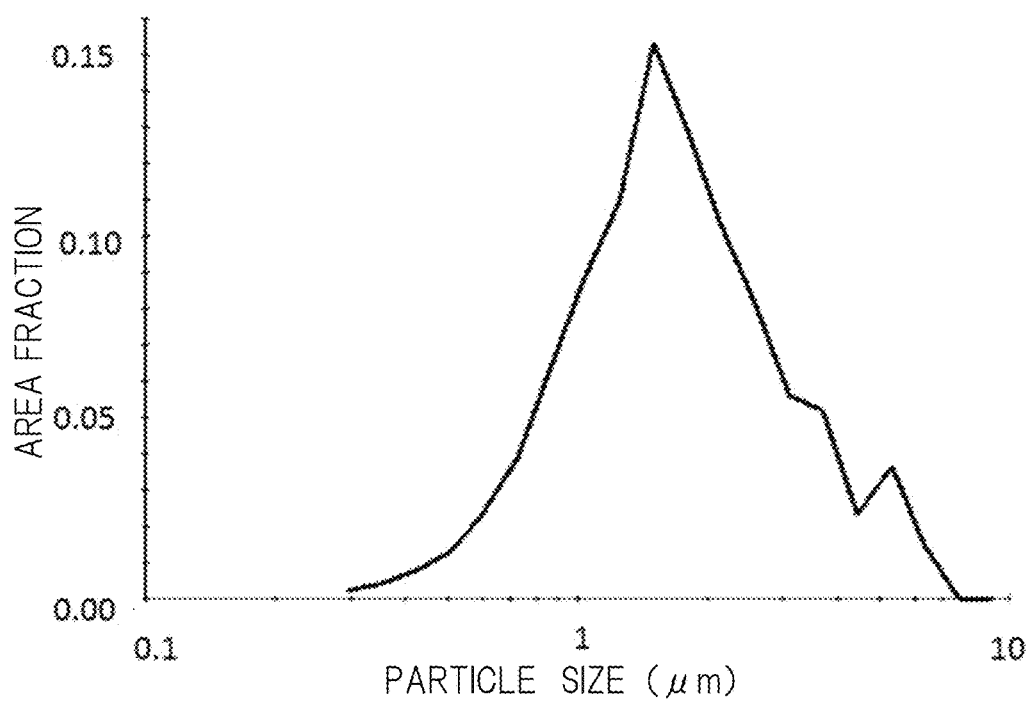
FIG. 4 shows a graph of a particle size distribution of a magnesium alloy according to Example 2 of the present invention.

A cross section of an extruded material of the alloy was cleaned by Ar ion beam sputtering and was observed using a scanning electron microscope (JSM-7000F manufactured by JEOL). From the observation, an average particle size was determined using electron back scattering diffraction (EBSD) technique, and a standard deviation of a particle size distribution was calculated. Table 2 shows the results, and FIG. 3 and FIG. 4 show graphs of particle size distributions. As for each sample, observation of precipitates was carried out over an observation region of 2 mm×2 mm, and no precipitate having a particle size of 100 nm or larger was found.

TABLE 2

| | Tensile strength (MPa) | Proof strength (MPa) | Elongation (%) | Average crystal particle size (μm) | Standard deviation |
|---|---|---|---|---|---|
| Example 1 | 288 | 213 | 38 | 1.97 | 0.62 |
| Example 2 | 297 | 217 | 27 | 1.97 | 0.63 |

The present invention provides a magnesium alloy which has an excellent deformation property and can prevent corrosion due to potential difference because the magnesium alloy includes a matrix phase which forms a single-phase solid solution. Thus, it is possible to suitably control a decomposition rate of the magnesium alloy in living tissues. For this reason, the magnesium alloy is highly applicable, for example, as a metal member for a medical device, such as stents and staplers, which involves deformation during use and requires stable biodegradability.

What is claimed is:

1. A magnesium alloy containing, in % by mass, 0.95 to 2.00% of Zn, 0.05% or more and less than 0.30% of Zr, 0.05 to 0.20% of Mn, and the balance consisting of Mg and unavoidable impurities, wherein
a total content of the unavoidable impurities is 30 ppm or less,
a content of each of Fe, Ni, Co, and Cu as unavoidable impurities is less than 10 ppm,
the magnesium alloy consists of a matrix phase consisting of single-phase solid solution and Zr-bearing precipitates dispersed in the matrix phase, wherein the particle size of the precipitates is smaller than 100 nm,
the matrix phase of the magnesium alloy has a particle size distribution with an average crystal particle size from 1.0 to 3.0 μm and a standard deviation of 0.7 or smaller, and
the magnesium alloy has a fracture elongation of 38% or more and a tensile strength from 288 to 300 MPa in a value measured in accordance with JIS Z2241.

2. The magnesium alloy as claimed in claim 1, wherein the magnesium alloy does not contain rare-earth elements and aluminum.

3. The magnesium alloy as claimed in claim 1, wherein the fracture elongation of the magnesium alloy is 50% or less in a value measured in accordance with JIS Z2241.

4. The magnesium alloy as claimed in claim 1, wherein the magnesium alloy has a proof strength from 145 to 220 MPa in values measured in accordance with JIS Z2241.

5. A medical device comprising a metal member including the magnesium alloy as claimed in claim 1.

\* \* \* \* \*

UNITED STATES PATENT AND TRADEMARK OFFICE
CERTIFICATE OF CORRECTION

| | |
|---|---|
| PATENT NO. | : 11,685,975 B2 |
| APPLICATION NO. | : 17/138492 |
| DATED | : June 27, 2023 |
| INVENTOR(S) | : Hironori Ueda, Masashi Inoue and Makoto Sasaki |

It is certified that error appears in the above-identified patent and that said Letters Patent is hereby corrected as shown below:

On the Title Page

Page 2, Item (56) References Cited FOREIGN PATENT DOCUMENTS:
"EP 03482947 A1 4/1992"
Should be:
-EP 0482947 A1 4/1992-

Signed and Sealed this
Sixth Day of February, 2024

Katherine Kelly Vidal
*Director of the United States Patent and Trademark Office*